United States Patent
Freeman

(10) Patent No.: US 10,874,315 B2
(45) Date of Patent: Dec. 29, 2020

(54) NON-INVASIVE BLOOD FLOW MEASUREMENT

(71) Applicant: ZOLL Medical Corporation, Chelmsford, MA (US)

(72) Inventor: Gary A. Freeman, Waltham, MA (US)

(73) Assignee: ZOLL Medical Corporation, Chelmsford, MA (US)

( * ) Notice: Subject to any disclaimer, the term of this patent is extended or adjusted under 35 U.S.C. 154(b) by 540 days.

(21) Appl. No.: 15/468,924

(22) Filed: Mar. 24, 2017

(65) Prior Publication Data
US 2017/0281023 A1   Oct. 5, 2017

Related U.S. Application Data

(60) Provisional application No. 62/315,150, filed on Mar. 30, 2016.

(51) Int. Cl.
*A61B 5/0265* (2006.01)
*A61B 5/00* (2006.01)
(Continued)

(52) U.S. Cl.
CPC .......... *A61B 5/0265* (2013.01); *A61B 5/0036* (2018.08); *A61B 5/4064* (2013.01); *A61B 5/4836* (2013.01); *A61B 5/6822* (2013.01); *A61B 5/6831* (2013.01); *A61B 7/04* (2013.01); *A61B 8/06* (2013.01); *A61B 8/0841* (2013.01); *A61B 8/0891* (2013.01);
(Continued)

(58) Field of Classification Search
CPC ... A61B 5/0265; A61B 5/4064; A61B 5/4836; A61B 5/6822; A61B 5/6831; A61B 7/04; A61B 8/06; A61B 8/0841; A61B 8/0891; A61B 8/4227; A61B 8/488; A61B 8/0808; A61B 2562/0223; A61B 2562/042; A61B 2562/063; A61N 1/025; A61N 1/39
See application file for complete search history.

(56) References Cited

U.S. PATENT DOCUMENTS 3,659,591 A * 5/1972 Doll ..................... A61B 5/0265
600/407
5,417,119 A   5/1995 Smoll
(Continued)

OTHER PUBLICATIONS

Bhatt, Bhargav et al., "Theoretical Analysis of Induced Potentials due to Blood flow under the Static Magnetic Field of MRI", Indian Journal of Biomechanics: Special Issue, (NCBM 7-8), Mar. 2009, 5 pages.
(Continued)

*Primary Examiner* — Peter Luong
(74) *Attorney, Agent, or Firm* — Fish & Richardson P.C.

(57) ABSTRACT

A system for determining blood flow to and from the brain of a patient includes a plurality of magnetic elements configured to be positioned adjacent to the neck of the patient and apply at least one magnetic field to the neck of the patient. The system includes a plurality of electrodes configured to be in electrical contact with the neck of the patient, the electrodes configured to detect a voltage induced across the neck of the patient responsive to the applied magnetic field and blood flow through the neck of the patient. The system includes a support component for holding the plurality of magnetic elements and the plurality of electrodes at the neck of the patient.

42 Claims, 10 Drawing Sheets

(51) Int. Cl.
    *A61N 1/02*     (2006.01)
    *A61N 1/39*     (2006.01)
    *A61B 7/04*     (2006.01)
    *A61B 8/06*     (2006.01)
    *A61B 8/08*     (2006.01)
    *A61B 8/00*     (2006.01)

(52) U.S. Cl.
    CPC ............ *A61B 8/4227* (2013.01); *A61B 8/488* (2013.01); *A61N 1/025* (2013.01); *A61N 1/39* (2013.01); *A61B 8/0808* (2013.01); *A61B 2562/0223* (2013.01); *A61B 2562/043* (2013.01); *A61B 2562/063* (2013.01)

(56) References Cited

U.S. PATENT DOCUMENTS

| | | | | |
|---|---|---|---|---|
| 2005/0054939 | A1* | 3/2005 | Ben-Ari ............... | A61B 5/0261 600/506 |
| 2011/0295083 | A1* | 12/2011 | Doelling ............... | A61B 5/103 600/301 |
| 2014/0039291 | A1 | 2/2014 | Freeman et al. | |

OTHER PUBLICATIONS

Cootes, Timothy F. et al., "Active Appearance Models", IEEE Transactions on Pattern Analysis and Machine Intelligence, vol. 23(6):681-685, Jun. 2001.

De Luca, R., "Lorentz force on sodium and chlorine ions in a salt water solution flow under a transverse magnetic field", Eur. J. Phys., vol. 30:459-466, 2009.

Dufour, Roger M. et al., "Template Matching Based Object Recognition With Unknown Geometric Parameters", IEEE Transactions on Image Processing, vol. 11(12):1385-1396, Dec. 2002.

Kinouchi, Y. et al., "Theoretical Analysis of Magnetic Field Interactions With Aortic Blood Flow", Bioelectromagnetics, vol. 17:21-32, 1996.

Krause, Jens, "Electromagnetic Flow Metering", www.intechopen.com, Jun. 1, 2008, 23 pages.

Shit, Gopal Chandra, Research Article "Computational Modelling of Blood flow Development and Its Characteristics in Magnetic Environment", Modelling and Simulation in Engineering, vol. 2013, 2013, 12 pages.

Vauhkonen, M. et al., A measurement system and image reconstruction in magnetic induction tomography, Physiol. Meas., vol. 29:S445-S454, 2008.

Wyatt, D. G., "Blood flow and blood velocity measurement in vivo by electromagnetic induction", Medical & Biological Engineering & Computing, vol. 22: 193-211, 1984.

Wyatt, D. G., "The electromagnetic blood flowmeter", Journal of Scientific Instruments (Journal of Physics E), vol. 1, Series 2, 1968.

Turovets et al., "Anatomically Constrained Conductivity Estimation of the Human Head Tissues in Vivo: Computational Procedure and Preliminary Experiments", IFMBE Proceeding, vol. 6: 3854-3857, 2006.

Wikipedia, Lorentz force, http://en.wikipedia.org/wiki/Lorentz_force, 17 pages, 2017.

* cited by examiner

NON-INVASIVE BLOOD FLOW MEASUREMENT

CLAIM OF PRIORITY

This application claims priority under 35 USC § 119(e) to U.S. Patent Application Ser. No. 62/315,150, filed on Mar. 30, 2016, the entire contents of which are hereby incorporated by reference.

TECHNICAL FIELD

This application relates to the non-invasive measurement of blood flow through vessels in living organisms.

BACKGROUND

Cardiopulmonary resuscitation (CPR) is a process by which one or more rescuers may provide chest compressions and ventilations to a patient who has suffered an adverse cardiac event—by popular terms, a heart attack. Chest compressions are an important element of CPR particularly during the first five to eight minutes after CPR efforts begin, because chest compressions help maintain circulation through the body and in the heart itself, which is the organ that can sustain the most damage from an adverse cardiac event. Generally, American Heart Association (AHA) CPR Guidelines define protocols according to which a rescuer is to apply the chest compressions in coordination with ventilations. For example, 2010 AHA Guidelines specify a ratio of 30:2 for compressions to ventilations, meaning thirty compressions for every two breaths; and a rate of around 100 compressions per minute. The 2015 AHA Guidelines specify a similar ratio of compressions to ventilations; and a rate of 100-120 compressions per minute.

CPR may be performed by a team of one or more rescuers, such as when the rescuers are professionals such as emergency medical technicians (EMTs) on an ambulance crew. One rescuer can provide the chest compressions and another can time the ventilations of the patient to match the chest compressions according to an appropriate CPR protocol. In some cases, ventilation can be provided via a ventilation bag that a rescuer squeezes or by mouth-to-mouth resuscitation. CPR can be performed in conjunction with providing shocks to the patient from an external defibrillator, such as an automatic external defibrillator (AED) that is designed to be used by laypeople AEDs often provide audible information or instructions to rescuers, such as "push harder" (when the rescuer is not performing chest compressions forcefully enough), "stop CPR," "stand back" (because a shock is about to be delivered), or other information or instructions. In determining how chest compressions are being performed, some defibrillators may obtain information from one or more accelerometers (such as an accelerometer in the CPR D PADZ®, CPR STAT PADZ®, and ONE STEP™ pads made by ZOLL Medical, Chelmsford, Mass.) that can be used to compute depths of chest compression, which can then be used to determine that the compressions are too shallow to be effective and thus to cause the verbal cue "push harder" to be spoken by the defibrillator.

Chest compressions or ventilation or both may also be provided mechanically, e.g., by automated devices. For example, the AUTOPULSE® non-invasive cardiac support pump (made by ZOLL MEDICAL) includes a back board and belt that wraps around a patient's chest. A motor in the backboard causes the belt to cycle between tightening and loosening around the patient's chest so as to provide chest compressions automatically and periodically. Automatic ventilation has been provided to people with various respiratory problems by means of devices like a cuirass, in the form of a shell that wraps around a patient's torso and applies negative pressure below their diaphragm, such as in the form of the HAYEK RTX respirator (Medivent International Ltd., London, UK).

Current guidelines for CPR state that chest compressions be performed to a target depth of 2.0 to 2.4 inches, or approximately 5 to 6 cm. This recommendation is based on the experience of early pioneers of CPR. These guidelines are described in "Cardiopulmonary Resuscitation" by Ornato, Peberdy, and the 2015 AHA Guidelines for CPR & ECC published in Circulation on Oct. 15, 2015, the contents of each of which are incorporated by reference herein in their entirety. There are little to no clinical data in humans that describe what happens to blood flow when chest compressions are between 0 and 1.5 inches (the effect of compressions that are more shallow than the target depth), when chest compressions are between 1.5 and 2 inches (how stable is the target region), or when chest compressions are greater than 2 inches (how much more blood flow can be enabled by deeper compressions and at what cost in complications). The vigor of manual chest compression may vary widely among rescuers and may progressively diminish as a given rescuer tires. The effects of these variations are unknown, but would be inconsequential only if the function relating blood flow to chest compression depth showed a broad plateau in the neighborhood of 1 to 2 inches.

In the only existing study of the relationship of blood pressure and flow during CPR to chest compression amplitude, small (6-12 kg) anesthetized dogs were resuscitated during 2-minute periods of electrically induced ventricular fibrillation (VF) and Thumper® CPR (3). Cardiac output was measured using a special indicator dilution method designed for accuracy during the low-flow conditions of CPR. Referring to FIG. 1, the results showed that cardiac output depended on chest compression amplitude. Measurable cardiac output occurred once chest compressions exceeded a threshold compression depth (x0) of between 1.5 and 3.0 cm. Cardiac output increased as a linear function of compression depth beyond the compression threshold. Below the threshold compression depth, no measurable cardiac output was present. The mean value of the threshold compression depth was 2.3 cm, a value very close to 1 inch (2.54 cm). A similar threshold of 1.8 cm of compression depth was found for measurable blood pressure in response to chest compression.

For chest compression depths greater than 2.5 cm relatively modest increases in chest compression depth caused relatively large increases in cardiac output. These observations are also supported by clinical experience. Experienced rescuers have learned that for some patients, 1 to 2 inches of sternal compression may be inadequate and a slightly greater degree of chest compression may be used to generate an adequate carotid or femoral pulse. Authorities suggest in the guidelines for basic life support that an appropriate sternal compression depth for a patient is best gauged by using the compression force that generates a palpable carotid or femoral pulse in the patient. Yet we know from physiology that palpable carotid or femoral pulses do not necessarily guarantee blood flow if the venous and arterial pulses are the same.

Current guidelines for compressions to a depth of 2.0 to 2.4 inches or 5 to 6 cm are supported by limited research data. However, the guidelines and associated teaching materials do not emphasize the depth of compression as a critical variable. Rather, they seem to imply that any degree of chest compression within the prescribed range is satisfactory. Such an interpretation would be rational if the true function relating cardiac output and compression depth were as shown in FIG. 2, curve A. This hypothetical function rises to a plateau, such that any degree of compression in the plateau region would be close to maximally effective.

Research data (e.g., the data shown in FIG. 1) indicate that the actual functional relationship between cardiac output and compression depth is more like that of curve B in FIG. 2. In this situation cardiac output (e.g., blood flow) is quite sensitive to small changes in sternal displacement, and for some displacements below a critical threshold value (2 cm in the example of FIG. 2), cardiac output is virtually zero.

Chest compressions can be monitored using an accelerometer incorporated into a chest compression pad of resuscitation products, such as the ZOLL AED Plus® automatic external defibrillator (ZOLL Medical). The signal from the accelerometer is doubly integrated to produce a measure of compression depth that is monitored by the AED Auditory feedback can be provided to the rescuer if the monitored chest compression depth falls outside the recommended range."

Currently, the American Heart Association (AHA) and the International Liaison Committee On Resuscitation (ILCOR) have proposed a generic recommendation for chest compression depth and ancillary parameters such as compression release (a measure of how "square" the compression waveform is). For example, the recommended compression depth is currently 2-2.4 inches and 100 compressions per minute for all adult patients, regardless of the size or physiologic status of the patient. Devices that alert rescuers if the chest compression depth falls outside the recommended range provide fixed prompting for all adult patients based on the compression depths and rates recommended by AHA, ILCOR or other standards organizations.

Blood flow is a function of factors such as patient size, patient weight, the level of epinephrine in the patient's bloodstream, or other factors. Fixed CPR feedback settings for compression depth and rate can thus result in large variations in actual blood flow during CPR for each individual patient.

SUMMARY

In an aspect, a system for determining blood flow to and from the brain of a patient includes at least one output generator configured to be positioned adjacent to the neck of the patient and apply an output to the neck of the patient; at least one sensor configured to be positioned adjacent to the neck of the patient, the at least one sensor configured to detect a signal responsive to the applied output and blood flow through the neck of the patient; and a support component for holding the at least one output generator and the at least one sensor at the neck of the patient.

Embodiments can include one or more of the following features.

The at least one output generator includes a plurality of magnetic elements configured to apply at least one magnetic field to the neck of the patient. The system includes a current source, and wherein the plurality of magnetic elements includes two or more magnetic coils configured to generate a magnetic field to the neck of the patient responsive to current supplied by the current source. The plurality of magnetic elements includes at least one pair of magnetic coils. The at least one pair of magnetic coils are configured to be located at diametrically opposite positions around the neck of the patient. The plurality of magnetic elements is configured to generate a magnetic field that is substantially spatially uniform across the neck of the patient. The plurality of magnetic elements is configured to generate a time-varying magnetic field. The time-varying magnetic field has a period of between about 10 and about 100 milliseconds.

At least one of the sensors is disposed between at least two of the plurality of magnetic elements.

The at least one sensor includes a plurality of electrodes configured to be in electrical contact with the neck of the patient. The plurality of electrodes includes three or more electrodes. The plurality of electrodes is configured to detect a voltage induced across the neck of the patient responsive to the applied output. One of the plurality of electrodes is configured to be used as a reference electrode while the remaining electrodes are configured to be current sources, the induced voltages being measured on each electrode while the current is being delivered. The system includes a processor, with memory, power supply and other processing components, the processor configured to estimate a distribution of the signal within the neck of the patient, and to estimate a blood flow through the neck based at least in part on the estimated distribution of the signal. The processor is configured to estimate a distribution of induced voltages within the neck of the patient, and to estimate the blood flow through the neck based at least in part on the estimated induced voltage distribution. The processor is configured to estimate blood flow from two or more blood vessels in the neck based at least in part on the estimated induced voltage distribution. The processor is configured to estimate at least a two-dimensional distribution of the induced voltage within the neck of the patient. The processor is configured to estimate a three-dimensional distribution of the induced voltage within the neck of the patient. The processor is configured to estimate net blood flow into the brain based at least in part on the estimated induced voltage distribution. The estimated net blood flow into the brain is based on a difference between estimated blood flowing into the brain and estimated blood flowing out of the brain. The processor is configured to determine a location of each of one or more blood vessels in the neck of the patient based on the induced voltage distribution. The processor is configured to determine the location of each of the one or more blood vessels based at least in part on an expected location of each of the one or more blood vessels. The processor is configured to determine the location of each of the one or more blood vessels based at least in part on an impedance distribution in the neck of the patient. The processor is configured to provide a tomographic image indicative of the impedance distribution in the neck of the patient. The tomographic image includes a plurality of pixels, each pixel having an intensity proportional to the velocity of blood flow through a portion of the neck of the patient corresponding to the pixel. The processor is configured to determine an instantaneous measure of blood flow through each of the one or more blood vessels. The processor is configured to determine an average measure of blood flow through each of the one or more blood vessels over a period of time. The period of time includes a duration of a chest compression or a portion of a chest compression applied to the chest of the patient. The system includes a defibrillator including at least one of the processor, memory, power supply and processing components. The system includes at least of a computing device, tablet, mobile device, PDA and cellular phone that includes at least one of the processor, memory, power supply and processing components.

The support component includes a flexible sheet configured to support the at least one output generator adjacent to the neck of the patient. The flexible sheet is configured to wrap around at least a portion of the neck and to be supported by the neck. The flexible sheet includes ends configured to attach to each other for the flexible sheet to form a collar.

The at least one sensor comprises at least one of an acoustic sensor and an ultrasound sensor.

The system includes a processor, with memory, power supply and other processing components, the processor configured to provide an image of blood flow through the neck of the patient based on the signal responsive to the applied output and blood flow through the neck of the patient.

In an aspect, a system for determining blood flow to and from the brain of a patient includes circuitry for controlling at least one output generator to apply an output to the neck of the patient; circuitry for sensing and measuring a signal detected by at least one sensor responsive to the applied output and blood flow through the neck of the patient; and a processor, with memory, power supply and other processing components, for estimating at least a two-dimensional distribution of the signal within the neck of the patient, and estimating a blood flow through the neck based at least in part on the estimated signal distribution.

Embodiments can include one or more of the following features.

The circuitry for controlling the at least one output generator comprises circuitry for controlling a plurality of magnetic elements configured to apply a magnetic field to the neck of the patient.

The circuitry for sensing and measuring the signal comprises circuitry for sensing and measuring an induced voltage across the neck of the patient detected by electrodes. The processor is for estimating at least a two-dimensional distribution of the induced voltage within the neck of the patient, and estimating a blood flow through the neck based at least in part on the estimated induced voltage distribution.

The processor is configured to estimate a three-dimensional distribution of the induced signal within the neck of the patient.

The processor is configured to estimate net blood flow into the brain based at least in part on the estimated signal distribution.

The processor is configured to determine a location of each of one or more blood vessels in the neck of the patient based on the signal distribution. The processor is configured to determine the location of each of the one or more blood vessels based at least in part on an impedance distribution in the neck of the patient. The processor is configured to provide a tomographic image indicative of the impedance distribution in the neck of the patient. The tomographic image includes a plurality of pixels, each pixel having an intensity proportional to the velocity of blood flow through a portion of the neck of the patient corresponding to the pixel.

The processor is configured to determine an instantaneous measure of blood flow through each of the one or more blood vessels.

The processor is configured to determine an average measure of blood flow through each of the one or more blood vessels over a period of time. The period of time includes a duration of a chest compression or a portion of a chest compression applied to the chest of the patient.

The system includes a defibrillator including at least one of the processor, memory, power supply and processing components.

The system includes at least one of a computing device, tablet, mobile device, PDA and cellular phone that includes at least one of the processor, memory, power supply and processing components.

Other features will be apparent from the drawings, detailed description, and claims.

DETAILED DESCRIPTION

Figure 1:
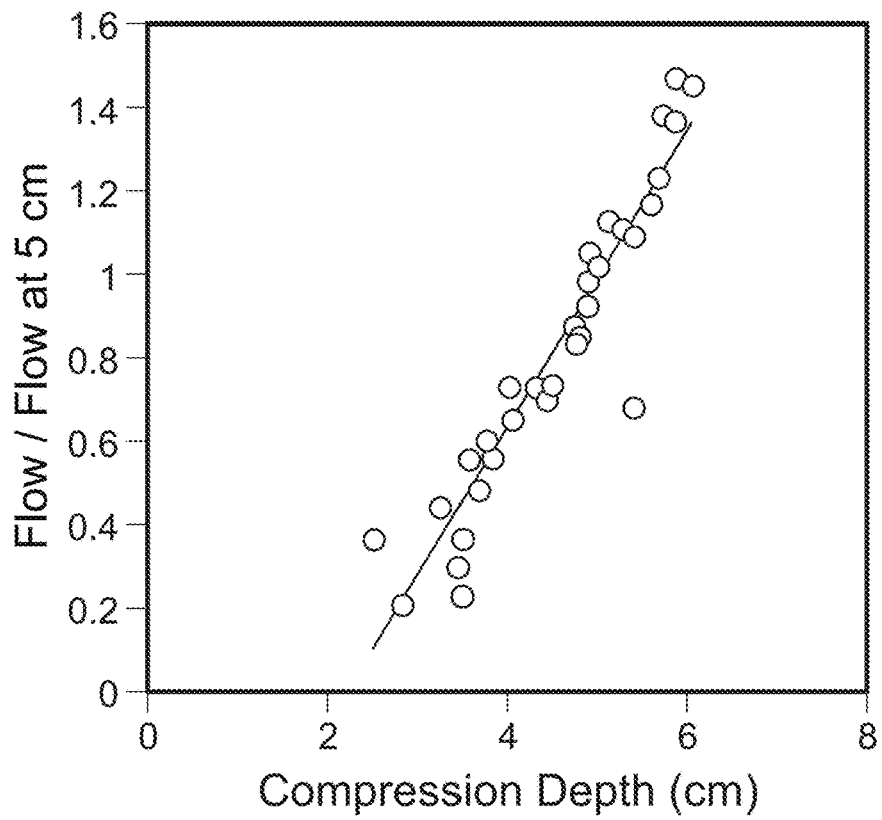
FIGS. 1 and 2 are plots of blood flow versus compression depth.
Figure 2:
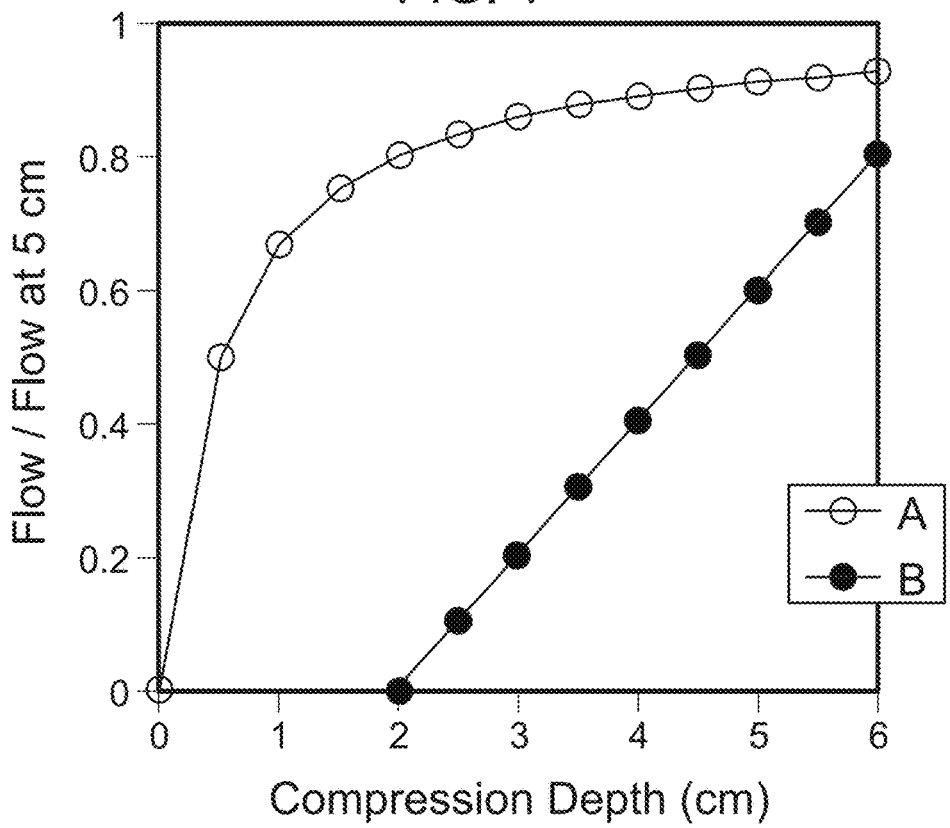

We describe here an approach to determine blood flow to and/or from the brain of a patient that can be performed during cardiopulmonary resuscitation (CPR). An indication of the blood flow to and/or from the brain can help CPR to be performed more effectively. For instance, if the blood flow to the brain is too low, a rescuer can be instructed to deliver deeper or more rapid CPR compressions to the patient in order to increase cardiac output. Or, if the blood flow to the brain is sufficient (e.g., above a certain threshold), the rescuer can be instructed to maintain the manner in which chest compressions are applied.

The present disclosure relates to systems for determining blood flow to and from the brain of a patient. Such systems may include one or more output generators that are configured to be positioned adjacent to the neck of the patient so as to be able to apply an output to the neck of the patient. One or more sensors may also be positioned adjacent to the neck of the patient and configured to detect a signal responsive to the applied output and blood flow through the neck of the patient. Any suitable output that can be sensed in combination with blood flow may be employed. For example, when a magnetic field is applied to the neck and blood having point charges therein flows through the neck at an appropriate orientation relative to the magnetic field, an electrical current may be generated. Hence, electrodes may be used to sense the electrical current produced from the interaction between the magnetic field and the blood flow. Alternatively, an appropriate level of acoustic (e.g., ultrasonic) energy may be provided to and/or measured from the neck of the patient based on the flow of blood through the neck. In some cases, the measurement of ultrasonic energy applied to and reflected from the neck of the patient may be used to determine how blood flows there through. Other systems for generating an output and sensing a signal responsive to the applied output and blood flow through the neck may be employed. A support component, such as a flexible sheet, collar, support strap, adhesive, etc. may be used to holding the output generator(s) and sensor(s) at the neck of the patient. In addition, using systems and methods described herein, blood flow through the neck of the patient may be imaged, for example, the amount of blood flowing through each blood vessel of the neck may be determined.

In certain embodiments, a system for determining or otherwise estimating blood flow may include an apparatus, such as a support component (e.g., collar) designed to be placed around the neck of a patient, or other support mechanism (e.g., flexible sheet, wearable patches, adhesive elements, amongst others). The apparatus may include one or more output generators, such as a number of magnetic elements, for example, located at diametrically opposite positions of the apparatus and configured to apply a magnetic field to the neck area of the patient. The apparatus may further include one or more sensors, such as electrodes configured to be in electrical contact with the neck of the patient, and further configured to detect a voltage induced across the neck of the patient responsive to the applied magnetic field and blood flow along the neck of the patient. As discussed further herein, since blood includes charged ions in solution, based on fundamental principles of electromagnetism, the movement of the charged ions relative to the applied magnetic field may produce a detectable voltage or force which may provide a reasonable indication of the amount of blood flow through the neck of the patient.

Figure 3:
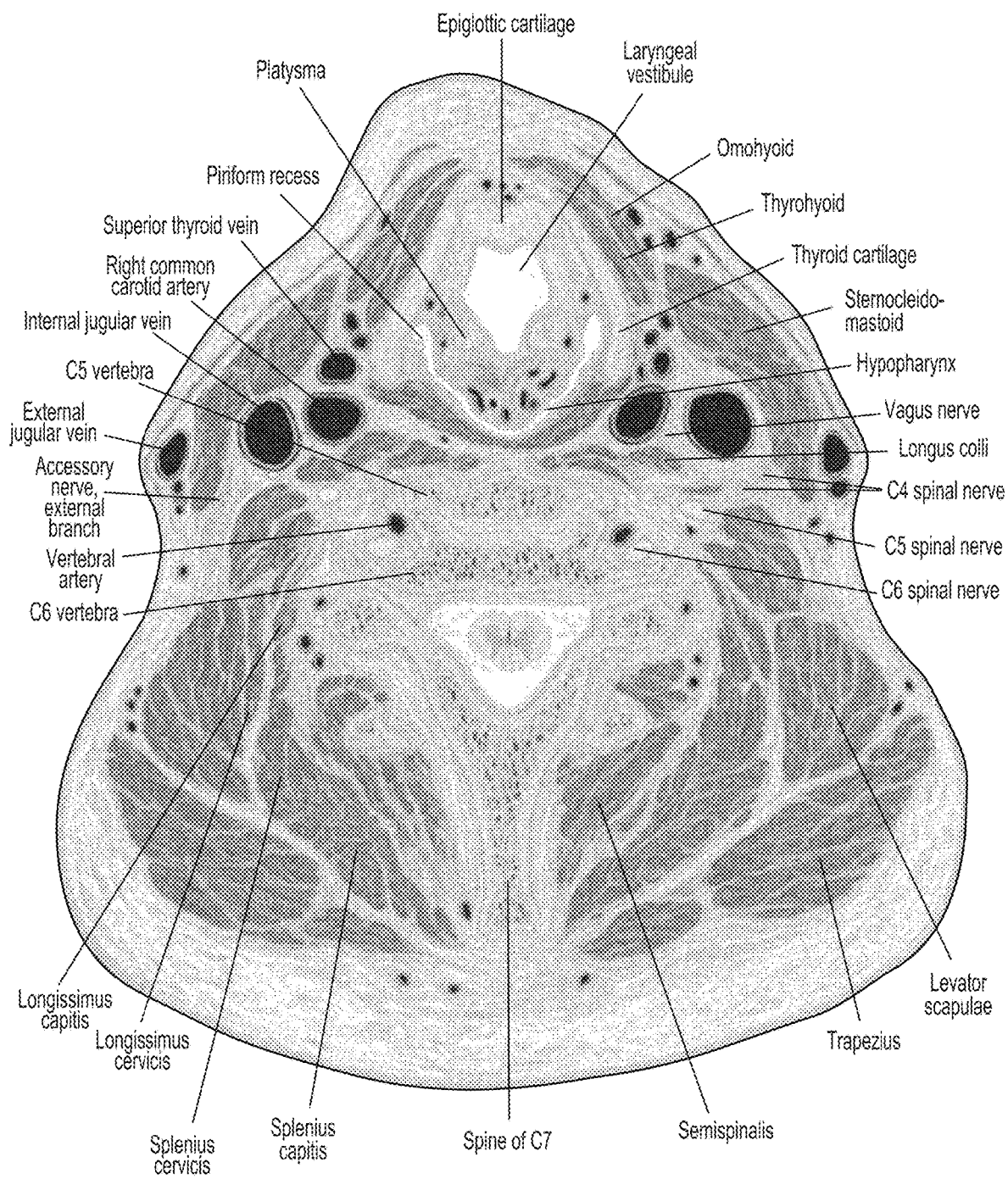
FIG. 3 is a cross sectional view of blood vessels in the neck.

Referring to FIG. 3, a large number of blood vessels carry blood to and from the brain, including the right and left common carotid arteries, the right and left internal carotid arteries, the right and left internal jugular veins, the right and left vertebral artery, the right and left external jugular vein, and other blood vessels. Some of these blood vessels supply blood to superficial aspects of the brain, such as the facial artery. Other blood vessels, such as the internal carotid and vertebral arteries and the internal and external jugular veins, have major clinical importance in supplying blood to the brain, such as via the circle of Willis.

Brain perfusion is the total blood flow to the brain. Brain perfusion can be determined by simultaneously measuring the blood flow through all of the blood vessels in the neck of a patient, individually calculating the blood flow into and out of each of the main vessels taking blood to and from the brain and summing the blood flow through each vessel to obtain the net blood flow to the brain. The blood flow into and out of particular vessels can be measured to assess regional perfusion, or the blood flow to a particular region of the brain.

In an approach described here, electromagnetic blood flow measurement is used for non-invasive measurement of blood flow to the brain of a patient. In an electromagnetic blood flow measurement, electric charges in a fluid (e.g., ions in blood in the arteries and veins in the neck of a patient) are displaced in response to an external magnetic field that is applied orthogonal to the direction of blood flow through the blood vessels. The charge separation leads to an electric field in each blood vessel, and hence an electric potential across the neck of the patient, which can be sensed with external electrodes. A tomographic image of the electric field generated in the neck of a patient responsive to the applied magnetic field may be created and provided to a user or machine for assisting diagnosis and/or treatment of the patient. In the tomographic image, the intensity of each pixel, or image element, is proportional to the velocity of blood flow through that element. The tomographic image can be analyzed in light of the locations of the blood vessels in the neck of the patient to provide an estimate of the flow rate through each of two or more individual blood vessels, and hence an estimate of the total flow of blood through the neck of the patient. We sometimes refer to this approach as Lorentzian Tomographic Flow (LTF) imaging.

Figure 4:
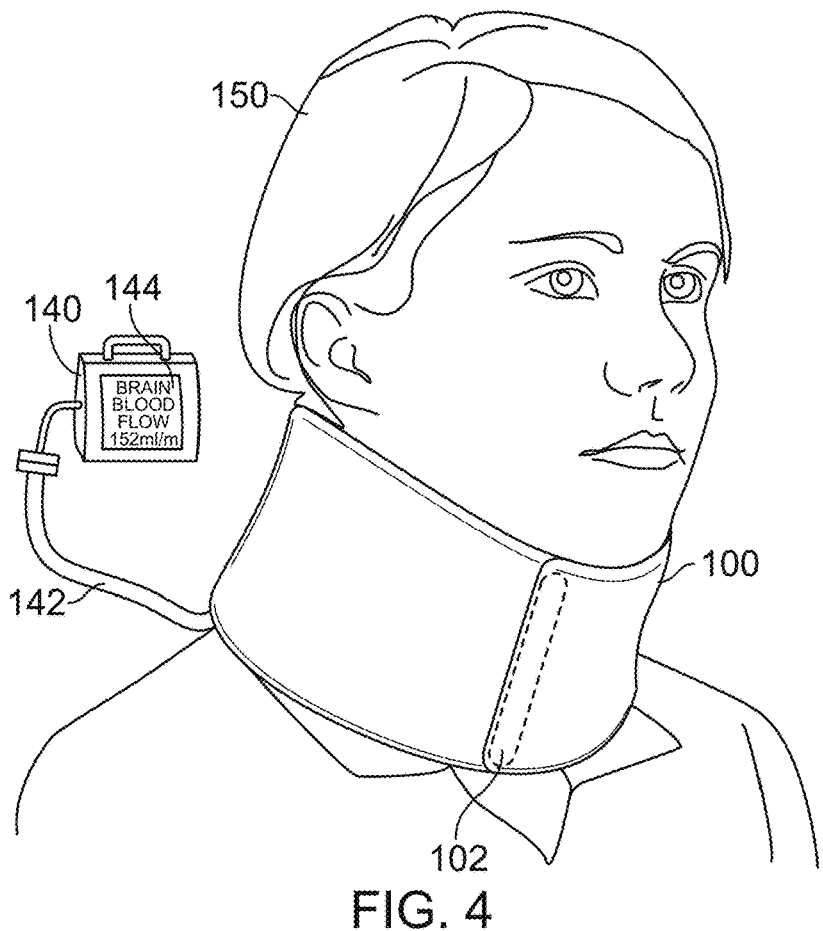
FIGS. 4 and 5 are diagrams of a collar.
Figure 5:
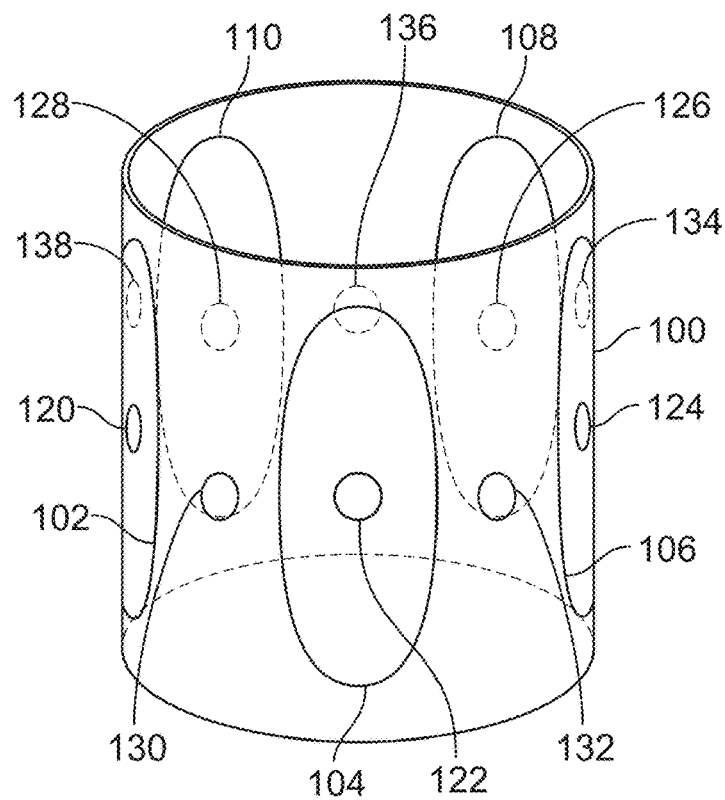

Referring to FIGS. 4 and 5, a flexible collar 100 can be placed around the neck of a patient 150, encircling the neck of the patient 150. The collar 100 includes magnetic elements that can apply a magnetic field to the neck of the patient 150 and electrodes to measure the resulting induced voltage across the neck of the patient. The collar 100 can be affixed by a closing mechanism, such as Velcro® 102, snaps, buttons, adhesive tape, or another appropriate closing mechanism, such that the collar 100 can be readily applied to or removed from the patient 150 in an emergency situation. For instance, the collar 100 can be used by a rescuer who is delivering CPR to a patient undergoing cardiac arrest.

The collar 100 houses multiple pairs of magnetic elements, such as magnetic-induction coils 102, 104, 106, 108, 110. The example collar 100 of FIG. 5 includes five coils. In some examples, the collar 100 can include a different number of coils, such as two coils, three coils, four coils, fix coils, seven coils, eight coils, sixteen coils, or another number of coils. In various embodiments, there may be an even or odd number of magnetic coils, arranged in pairs. For example, for an even number of coils, the coils may be provided as separate pairs; for an odd number of coils, one or more coils may be included in multiple pairs. A larger number of coils can improve the resolution of the system. In some examples, the coils are positioned on the collar 100 such that, when the collar is placed around the neck of the patient 150, each coil is approximately diametrically opposed to another coil around the circumference of the collar 100.

More generally, the magnetic coils can be supported around the neck of the patient 150 by a support component, such as a flexible sheet of material that is configured to wrap around at least a portion of the neck of the patient 150. The flexible sheet of material can have ends that are configured to attach to each other by a closing mechanism, such as Velcro® 102, snaps, buttons, adhesive tape, or another appropriate closing mechanism, in order to secure the flexible sheet of material around the neck. The magnetic coils can be disposed in pockets of the flexible sheet, or can be attached to the flexible sheet of material, e.g., via stitching, stables, or another attachment mechanism.

When energized, the magnetic coils apply a magnetic field to the neck of the patient 150. The magnetic field can be a static magnetic field or a time-varying magnetic field. Application of a magnetic field to the neck of the patient in the presence of blood flow through the neck may induce a voltage in the blood vessels in the neck, which can be measured and used to determine the amount of blood flow through the neck, as discussed further below.

In some versions, the individual magnetic coils may be circularly-wound coils, such as open-core or magnetic core coils, approximately 50×50×50 mm in size, potted with substance such as epoxy or more compliant silicone materials, known to those skilled in the art. In some versions, the coils are capable of generating a magnetic field of about 0.02 Tesla at a distance of approximately 1 cm from the coil. In some versions, the field may be as low as 0.005 Tesla or as high as 1 Tesla. Low resistance coil wire, such as superconducting wire, can be used to generate high magnetic fields such as 1 Tesla.

Figure 6:
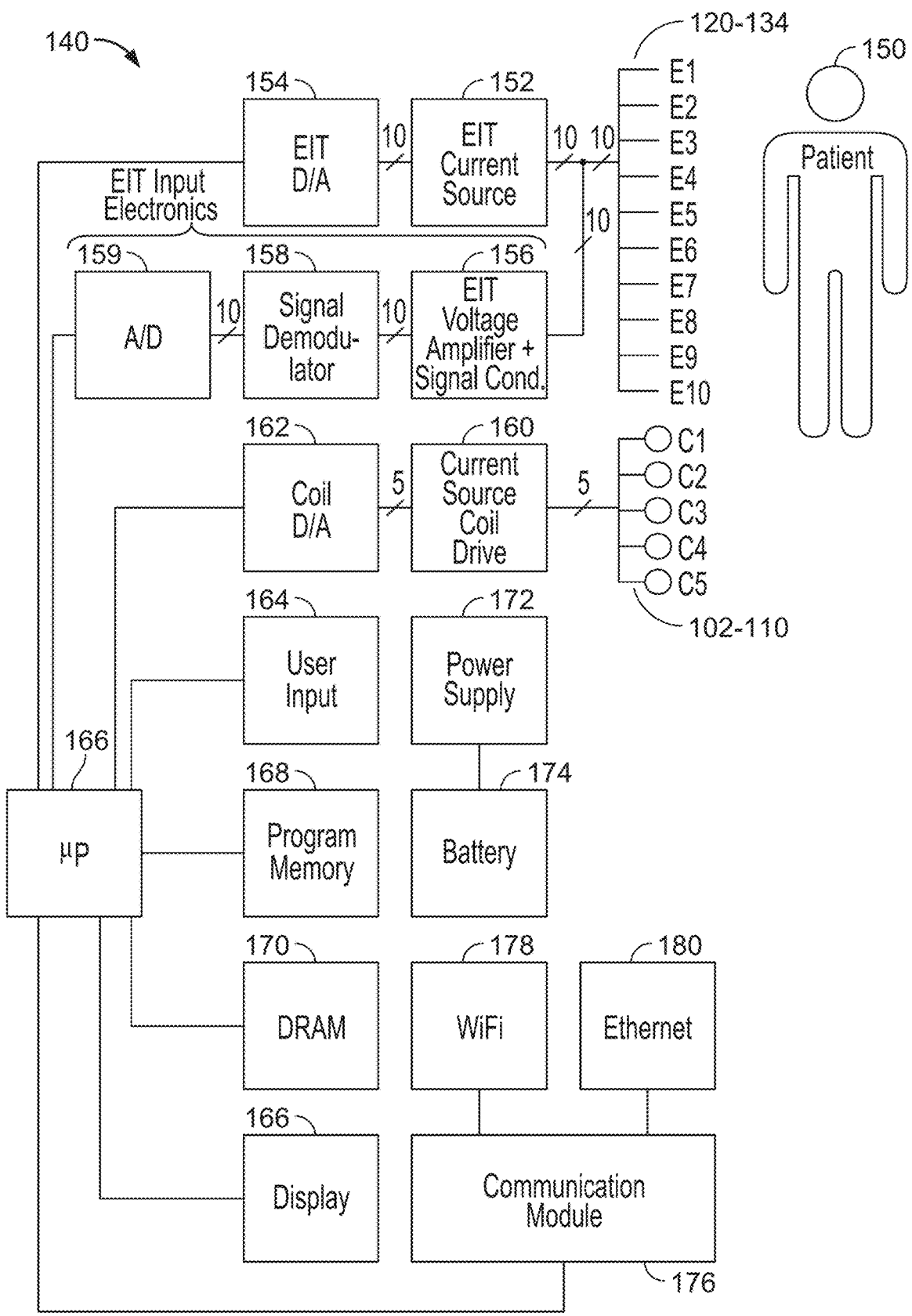
FIG. 6 is a block diagram of a control system.

Referring also to FIG. 6, the coils 102-110 are controlled by driver electronics that are housed in a control device 140a current source to the coils 102-110. For instance, the driver electronics 160, 162 can deliver an approximately square wave alternating current to the coils 102-110, causing the coils to generate a magnetic field that is applied to the neck of the patient. In some examples, diametrically opposed coils are driven simultaneously by the driver electronics 160, 162 to generate a magnetic field that is relatively spatially-uniform across the neck of the patient 150. The driving frequency may be between 30 Hz and 1000 Hz, such as about 400 Hz. The number of interconnects that connect components of the electronic block diagram may be indicated by a number (e.g., 5, 10, or another number) located over a slash, as provided in FIG. 6 and known to those of ordinary skill in the art.

Multiple electrodes may be positioned on an inside surface of the collar 100, or other support apparatus, such that, when the collar 100 is placed around the neck of the patient 150, the electrodes are in electrical contact with the skin of the neck. A voltage between two electrodes is detected, such as a voltage induced in the blood vessels in the neck by the magnetic field applied to the neck by the coils. For instance, the voltage between an electrode and another, diametrically opposed electrode can be detected. The collar 100 can include the same number of electrodes and coils, more electrodes than coils, or more coils than electrodes. A larger number of electrodes enables higher resolution measurement of the voltage distribution around the neck of the patient.

In the example of FIG. 5, each of electrodes 120, 122, 124, 126, and 128 is approximately centered in a corresponding one of the coils 102-110. Each of electrodes 130, 132, 134, 136 and 138 is located in between two adjacent coils 102-110. The electrodes can be standard, commercial ECG electrodes, such as those manufactured by ZOLL Medical (Chelmsford, Mass.). The size of these electrodes is typically 1" in diameter, and the electrodes can be composed of a conductive gel, a metallic contact region, some dielectric foam and an electrical connector. In some examples, one or more rows of electrodes (not shown) can be positioned above or below the coils, such as a row of electrodes spaced by 0.25 inches, 0.5 inches, 1.0 inches, or by another distance. The collar 100 can include electrodes centered in the coils, electrodes located in between adjacent coils, rows of electrodes above or below the coils, or a combination of any two or more of them.

In examples where the coils 102-110 apply a time-varying magnetic field to the neck of the patient 150, the driving frequency for the magnetic field can have a frequency of approximately 400 Hz, and as low as 10 Hz and as high as 1000 Hz, or a period of between about 10 milliseconds and about 100 milliseconds. The voltage generated across each pair of diametrically opposed electrodes is sampled and measured simultaneously with the voltage measurement by each other pair of diametrically opposed electrodes and synchronous with the driving frequency of the coils 102-110. Simultaneous, synchronous measurement allows synchronous modulation/demodulation to be performed to reduce or minimize noise or other interference effects in the electrical signal measured by the electrodes. The voltages generated may typically be in the range of approximately 0.5 µV-10 mV.

Figure 7:
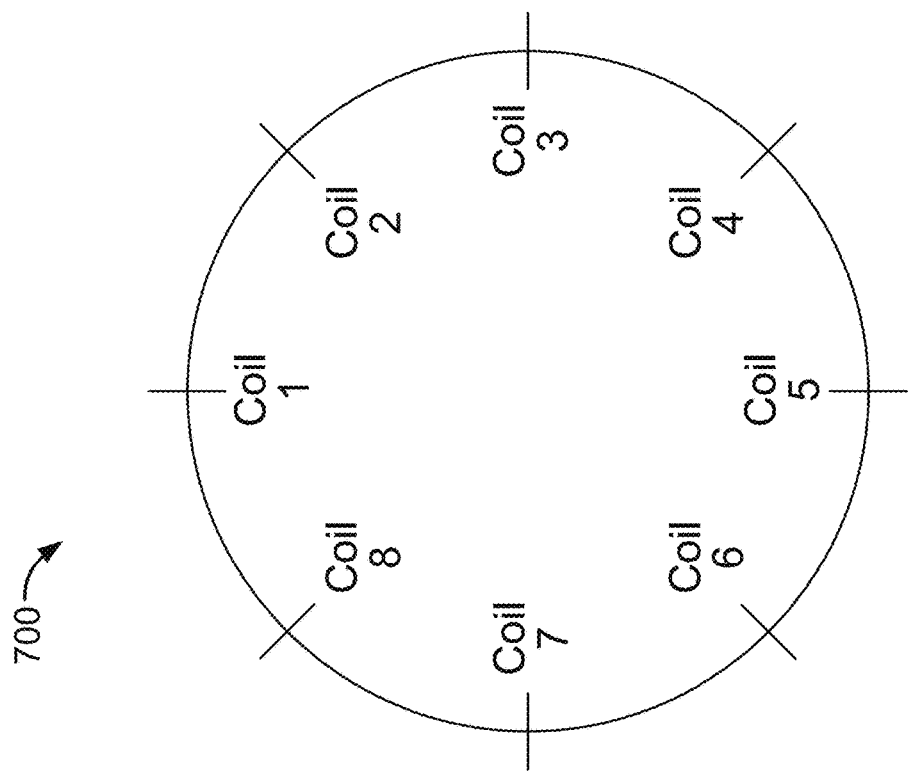
FIG. 7 is a diagram of a collar.

In some examples, such as when the collar includes more than four coils, subsets of the coils, such as groups of four coils, can be activated to create a wider, more uniform magnetic field. For instance, referring to FIG. 7, in a collar 700 having eight coils, coil-pair 1-2 is diametrically opposite to coil-pair 5-6. A drive pulse is applied to coil-pairs 1-2 and 5-6 to generate a magnetic field between the two pairs and voltages are synchronously measured, for instance between the electrodes associated with the coils 1, 2, 5, and 6. The drive pulse is then sequenced to the next subset of diametrically opposed coil pairs 2-3 and 6-7, and voltages are synchronously measured. This process is repeated for coil-pairs 3-4 and 7-8 and then for coil-pairs 4-5 and 8-1.

The measurement of a voltage induced in a blood vessel by application of a magnetic field is sometimes referred to as electromagnetic blood flow measurement, which can be used for both invasive and non-invasive measurement of blood flow in single vessels (as described in DG Wyatt, Journal of Scientific Instruments (Journal of Physics E) 1968 Series 2, Vol. 1, the contents of which are incorporated herein by reference in their entirety). In an electromagnetic blood flow measurement, electric charges in a fluid (such as ion-filled blood in the arteries and veins) are displaced due to the Lorentz-force in response to an external magnetic field applied orthogonal to the direction of fluid flow.

The Lorentz force is the force on a point charge due to an electromagnetic field applied to the point charge (sometimes also referred to as a particle or an ion). The Lorentz force F on a particle is given by the following equation in terms of the electric field (E) and the magnetic field (B) applied to the particle (Equation 1):

$$F=q(E+v\times B),$$

where
F is the force (in Newtons)
E is the electric field (in Volts per meter)
B is the magnetic field (in Tesla)
q is the electric charge of the particle (in Coulombs)
v is the instantaneous velocity of the particle (in meters per second)
× is the vector cross product
The Lorentz force may also be expressed as (Equation 2):

$$F = q\left(-\nabla\phi - \frac{\partial A}{\partial t} + v \times (\nabla \times A)\right).$$

Figure 8:
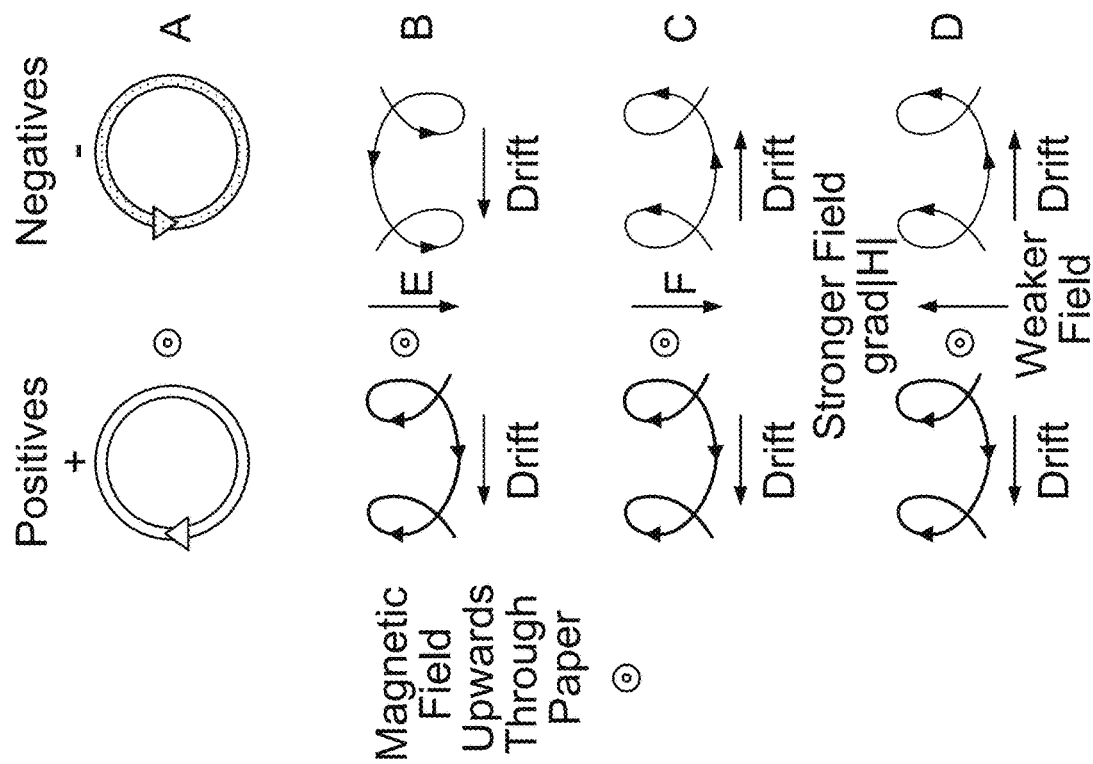
FIG. 8 is a schematic diagram of the effect of a transverse magnetic field on the motion of positive and negative charges.

Referring to FIG. 8, blood contains both positively charged ions and negatively charged ions in solution. The direction of the vector of the induced Lorentz force on a positively charged ion is opposite to the direction of the vector of the induced Lorentz force on a negatively charged ion, thus causing positively charged ions and negatively charged ions to move in opposite directions and resulting in segregation of the positively charged ions and the negatively charged ions.

The segregation of oppositely charged ions results in the creation of an electric dipole moment. The electric dipole moment p between two point charges, one with charge +q and the other one with charge −, q, is:

$$p=qd,$$

where d is the vector displacement pointing from the negative charge to the positive charge. The electric dipole moment vector p points from the negative charge to the positive charge. An idealization of this two-charge system is the electrical point dipole consisting of two (infinite) charges only infinitesimally separated, but with a finite p.

For a system of charges with no net charge, such as a system with a pair of opposite charges or a system with a neutral conductor in a uniform electric field, visualized as an array of paired opposite charges, the electric dipole moment is:

$$p(r) = \sum_{i=1}^{N} \int_V q_i [\delta(r_0 - (r_i + d_i)) - \delta(r_0 - r_i)](r_0 - r)d^3r_0$$

$$= \sum_{i=1}^{N} q_i [r_i + d_i - r - (r_i - r)]$$

$$= \sum_{i=1}^{N} q_i d_i = \sum_{i=1}^{N} p_i,$$

where p(r) is the electric dipole moment of the overall system as a function of the position r of an observer, $r_0$ is the initial position $r_i$ is the position of the ith charge pair, and $d_i$ is the vector displacement pointing from the negative charge to the positive charge in the ith charge pair. This expression for the electric dipole moment of the system is the vector sum of the individual dipole moment of each of the neutral charge pairs in the system. Because of the assumption of overall charge neutrality, the dipole moment is independent of the observer's position r. This expression shows that the electric dipole moment of a system with no net charge is independent of the choice of reference point.

Blood is an ionic solution containing both positive and negative ions which are segregated responsive to application of an electromagnetic field, as discussed above. This segregation of ions causes an electric dipole moment to be generated. In a blood vessel, the segregation of ions in blood induces a voltage, which can be measured and used to determine the blood flow through the blood vessel.

Figure 10:
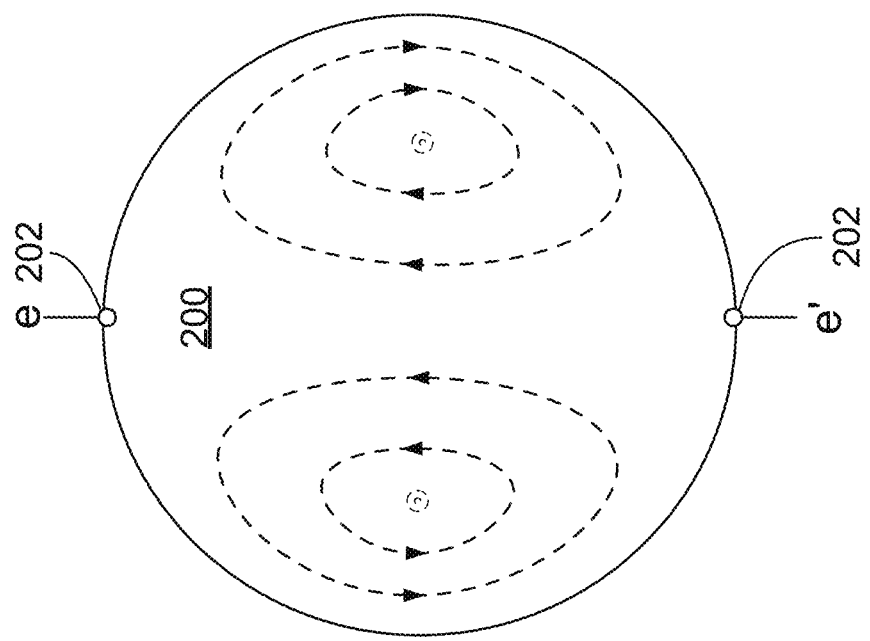
FIG. 10 is a cross-sectional diagram of a blood vessel.
Figure 9:
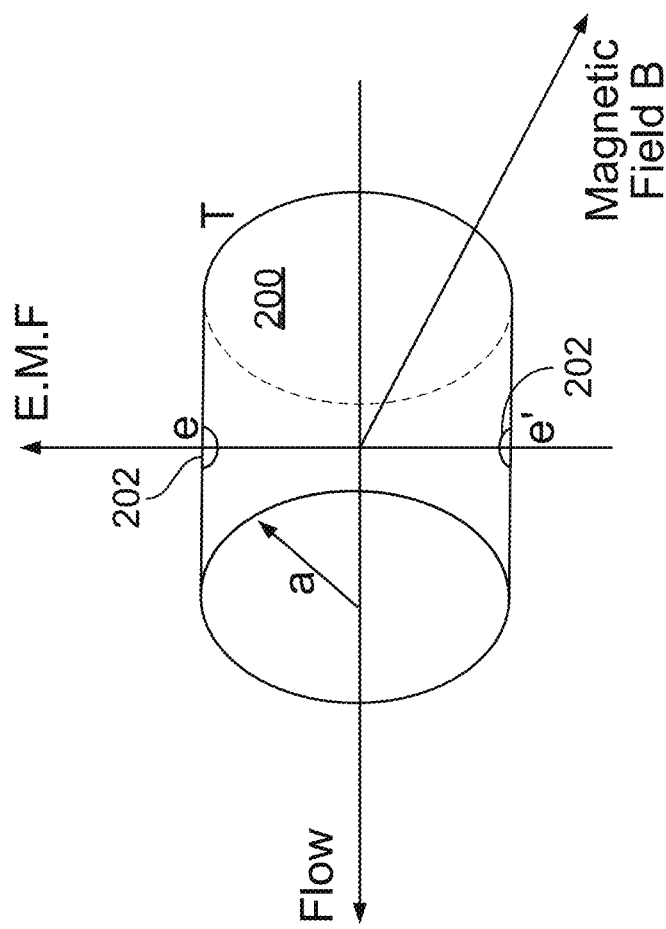
FIG. 9 is a schematic diagram of electromagnetic measurement of blood flow.

Referring to FIGS. 9 and 10, for measurement of blood flow through a single blood vessel 200, a uniform magnetic field B is applied perpendicular to both the longitudinal axis of the blood vessel 200 and the diameter of electrode 202 positioned on diametrically opposed sides of the blood vessel 200 (FIG. 9). Vectorially opposite Lorentz forces are induced on the positively and negatively charged ions in the blood in the blood vessel 200 as a result of the transverse magnetic field B. Because blood flow is constrained volumetrically by the walls 204 of the blood vessel 200, the opposite forces induced on the positively and negatively charged ions in turn, result in oppositely charged ions preferentially moving along opposite sides of the inner walls of the blood vessel 200. For instance, as shown in the cross sectional view of the blood vessel 200 (FIG. 10), positively charged ions and negatively charged ions are segregated into two flow patterns on opposite sides of the inner walls of the blood vessel 200. This segregation of oppositely charged ions results in an electric dipole moment and thus the generation of a voltage across the blood vessel 200.

In general, the fluid velocity in the blood vessel 200 is greater in the central region of the blood vessel 200 than near the inner walls of the blood vessel 200, and as a consequence higher central electromagnetic field (EMF) circulating currents flow in planes normal to the longitudinal axis of the blood vessel 200 (FIG. 10). The result is that the potential U between the electrodes 202 is not simply the sum of the induced EMFs between the electrodes 202, but rather the sum of the induced EMFs less an ohmic drop due to the circulating currents and the fluid resistance of the blood flowing through the blood vessel. When the velocity is uniform the induced electric force also is uniform and no circulating currents exist. In this case, corresponding to fully turbulent flow of velocity v, U=2aBZ" (from Wyatt).

The vector form of the relationship between the magnetic field applied to a blood vessel and the resulting voltage induced in the blood vessel is:

$$Ui=(v \times B) \cdot L,$$

where
Ui=induced voltage in the blood vessel (vector)
B=magnetic field applied to the blood vessel (vector)
L=length of the blood vessel, and
v=blood flow velocity in the blood vessel (vector).

Thus, by applying a magnetic field to a blood vessel of known length and measuring the voltage induced in that blood vessel, the blood flow velocity through the blood vessel can be determined.

The charge redistribution on moving blood in a blood vessel due to the application of a transverse magnetic field can also be described via the magnetohydrodynamic (MHD) effect, in which a finite element analysis is employed utilizing Maxwell's equation (Eq. 2 above) and the Navier-Stokes equations:

$$\rho(\partial \vec{v}/\partial t + \vec{v} \cdot \nabla \vec{v}) = (1/\mu)(\nabla \times \underline{B} \times \underline{B}) - \nabla p + \eta \nabla^2 \underline{v},$$

where ρ is the density of the blood, η is the viscosity coefficient of the blood, and p is the blood pressure in the blood vessel.

Referring again to FIGS. 4 and 5, the magnetic field applied to the neck by the coils 102-110 on the collar 100 induces Lorentz forces on the ionic charges in the blood flowing through the blood vessels in the neck. As a result, oppositely charged ionic charges in the blood separate out within each of the blood vessels in the neck, as discussed above, giving rise to a voltage across each blood vessel. The degree to which the oppositely charged ions separate in a given blood vessel and the magnitude of the resulting voltage across the blood vessel are a function of the intensity of the magnetic field applied to the neck and the velocity of the blood within the blood vessel. Thus, by applying a magnetic field of known intensity to the neck and determining the voltage induced across a given blood vessel, the blood flow velocity through the blood vessel can be determined. The total brain perfusion, or total blood flow to the brain, can then be determined by summing the blood flow through each of the individual blood vessels in the neck.

The electrodes 120-128, 130-138 measure the voltage at the surface of the neck, which is a function of the voltage across each individual blood vessel in the neck. The voltage measured at the surface of the neck by the electrodes is affected by factors such as the shape and location of each individual blood vessel in the neck and by the locations and conductivities or impedances of the various tissues in the neck that surround the blood vessels and that are present in the intervening space between the blood vessels and the electrodes. By determining the distribution of impedance in the neck of a patient, the voltage at the surface of the neck can be related to the internal voltage distribution in the neck. Based on an understanding of the location of individual blood vessels in the neck, the internal voltage distribution can then be used to determine the blood flow through each individual blood vessel in the neck, and hence the total brain perfusion in the patient. Electrical impedance tomography (EIT) is used to determine the internal conductance or impedance of living tissue. EIT is described in "Electrical Impedance Tomography" by J G Webster, 1990, and "Electrical Impedance Tomography" by D S Holder 2005, the contents of both of which are incorporated herein by reference in their entirety.

Figure 11:
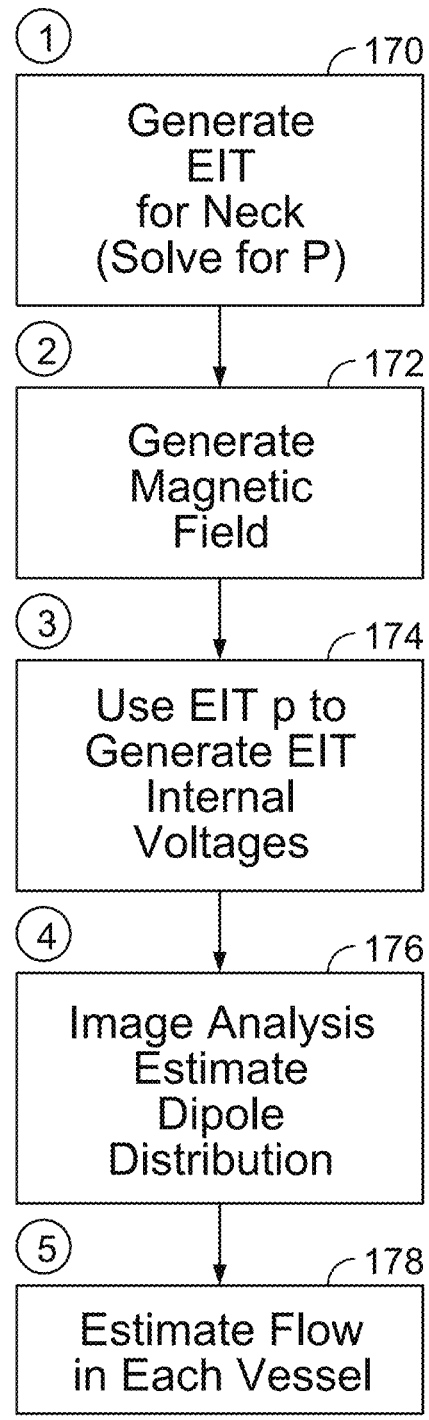
FIG. 11 is a flow chart.

Referring to FIG. 11, EIT is used to determine the impedance distribution (ρ) in the neck in at least two dimensions (170). The EIT is governed by Poisson's equation:

$$\nabla \cdot \rho^{-1} \nabla V = I,$$

where V is the voltage, ρ is the resistivity distribution, and I is the impressed current source distributions within the region being studied, and the boundary conditions are $V_0$ and $J_0$. In the case of EIT, high frequency, low amplitude signals, e.g., 60 KHz and ~1 microampere, respectively, are applied as a current source to the region being studied (e.g., the neck of the patient). Since there are no current sources of this frequency in the body, then ρ=0, and Poisson's equation becomes Laplace's equation:

$$\nabla \cdot \rho^{-1} \nabla V = 0$$

In the field of EIT, several types of problems can be studied:
1. The "forward problem," where ρ, $V_0$, and $J_0$ are given and the goal is to determine the voltage and current distributions V and J.
2. The "inverse problem," where V and J are given and the goal is to determine ρ.
3. The "boundary value problem," where $V_0$ and $J_0$ are given and the goal is to determine ρ, V, and J.

The determination of the impedance distribution (ρ) in the neck is an EIT "inverse" problem, solving for ρ. Refer ring again to FIGS. 4-6, the process of EIT involves injecting a current onto the surface of the neck of the patient 150 through the electrodes 120-128, 130-138 on the collar 100. Current is provided to the electrodes 120-128, 130-138 via microprocessor 166 control of EIT current-generating circuitry, which includes a D/A converter 154 and a current source 152 electrically connected to the electrodes. Injection of current onto the surface of the neck of the patient 150 through one or more the electrodes gives rise to an induced voltage, which is measured by one or more of the electrodes using EIT voltage amplifier and signal conditioning circuitry 156, a signal demodulator 158, and an analog to digital converter (A/D) 159. The measured induced voltages as a function of position on the surface of the neck are used to determine the impedance distribution through the neck.

In some examples, the "multireference method" is used for configuring the current voltage pairs. Further description of the multireference method can be found in Hua P, Webster J G, Tompkins W J 1987 Effect of the Measurement Method on Noise Handling and Image Quality of EIT Imaging, Proc. Annu. Int. Conf. IEEE Engineering in Medicine and Biology Society 9 1429-1430, the contents of which are incorporated herein by reference in their entirety. In the multireference method, one electrode is used as the reference electrode while the remaining electrodes act as current sources (sometimes also referred to as driving electrodes). The induced voltages are measured on each electrode simultaneously while the current is being delivered. The amplitude of the current sources is varied individually and each electrode is treated as a reference electrode in succession. Finite element methods are used to convert the calculus problem ($\nabla \cdot \rho^{-1} \nabla V = 0$) into a linear algebra problem of the form YV=C, where Y, V, and C are the conductance, voltage, and current matrices, respectively. Y, V, and C are also sometimes known as the master matrix, node voltage vector, and node current vector, respectively. Mesh generation is performed on a two or three-dimensional physical model with triangular or quadrilateral elements for two-dimensional problems and hexahedral elements for three-dimensional problems. Boundary conditions are set, such as at the reference electrode or driving electrodes. Example boundary conditions can include, for instance, the Dirichlet boundary condition (in which the surface voltages are known) or the Neuman boundary condition (in which the surface currents are known). The master matrix can be computed using any of a variety of methods, such as Gaussian elimination or Cholesky factorization.

In some examples, the Newton-Raphson algorithm can be used for reconstruction of the resistivity distribution (which is related to the impedance distribution) in the neck of the patient. This algorithm is an iterative algorithm that is well suited to non-linear problems. The Newton-Raphson method minimizes an error termed the "objective function," which is defined as the equally weighted mean square difference between the measured and estimated voltage responses:

$$\Phi(\rho) = (1/2)(V_e(\rho) - V_0)^T (V_e(\rho) - V_0).$$

According to the Newton-Raphson algorithm, a resistivity distribution is first estimated, then the theoretical voltage response to a given current input is calculated based on the estimated resistivity distribution, e.g., using a finite element method or another approach. The calculated voltages are subtracted from actual voltages measured responsive to the same current input to obtain an objective function. If the objective function is less than an error threshold, the estimated resistivity distribution is deemed to be an acceptable estimation. If not, the following equation is used to update the estimated resistivity distribution:

$$\Delta \rho^k = -[V_e'(\rho^k)^T V_e'(\rho^k)]^{-1} \{V_e'(\rho^k)^T [V_e'(\rho^k) - V_0]\}$$

This sequence is repeated iteratively until an acceptable estimation for the resistivity distribution is achieved.

In some examples, a table lookup method can be used to determine the estimated voltage matrix $V_e(\rho)$ used in the Newton-Raphson algorithm. The values in the lookup table can be based on average patient resistivity distributions and assuming correct placement of the electrodes.

The accuracy of the determined impedance or resistivity distribution can be improved by using a secondary imaging method such as ultrasound in combination with the measured current-voltage response of the neck. The high imaging resolution of ultrasound imaging enables the positions of the internal organs or tissues in the neck relative to the electrodes to be quantitatively determined. For instance, when the positions of internal organs or tissues are determined using a secondary imaging method, the EIT approach described above can be used to determine the impedance of each organ or tissue.

In some examples, an average impedance value can be determined for one or more tissue regions identified by the secondary imaging method. This is accomplished by first defining a tissue region in the neck, such as the vertebrae, esophagus, muscles, or other tissue regions, e.g., by image processing of the secondary image. The impedance or resistivity distribution calculated via the EIT method described above is overlaid onto the secondary image. All nodes of the impedance or resistivity distribution that are contained within a particular tissue region are combined together into a single impedance or resistivity measure for that tissue region. The method of combination may be an averaging, median, or other statistical or image processing method.

Referring again to FIG. 11, after the impedance distribution in the neck has been determined, a transverse magnetic field is generated (172) using the driver electronics 160, 162 as a current source for the coils 102-110. The application of a magnetic field to the neck induces a voltage across electrodes 120-128, 130-138 and measured via the EIT voltage amplifier and signal conditioning circuitry 156, the signal demodulator 158, and the A/D converter 159. Based on the voltages induced across the electrodes and the determined impedance distribution in the neck, the internal voltage distributions in the neck, such as a two-dimensional or three-dimensional internal voltage distribution, can be calculated, e.g., using the boundary value approach described above (174).

Figure 12:
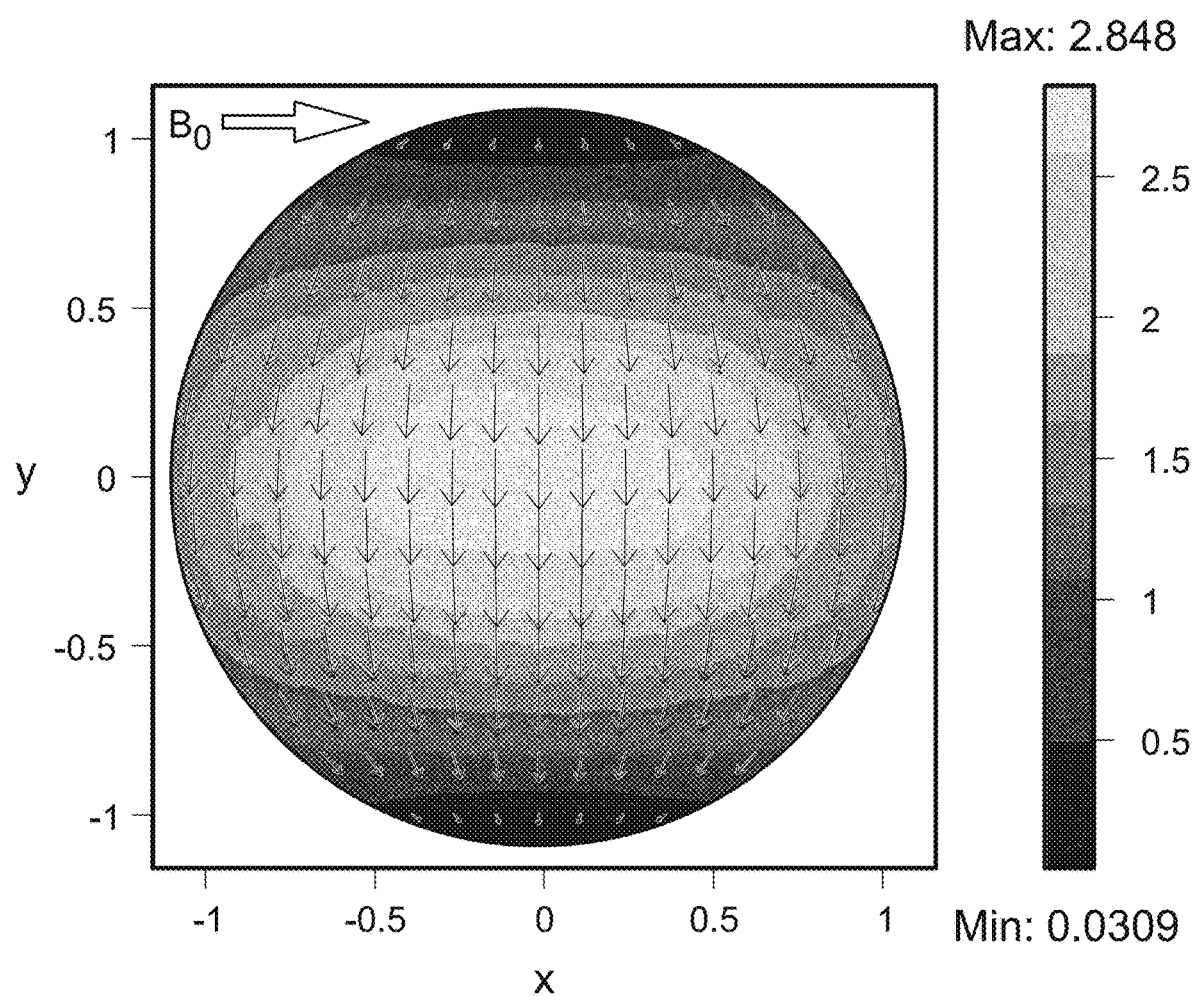
FIG. 12 is a cross-sectional view of the distribution of electric fields in a blood vessel.
Figure 13:
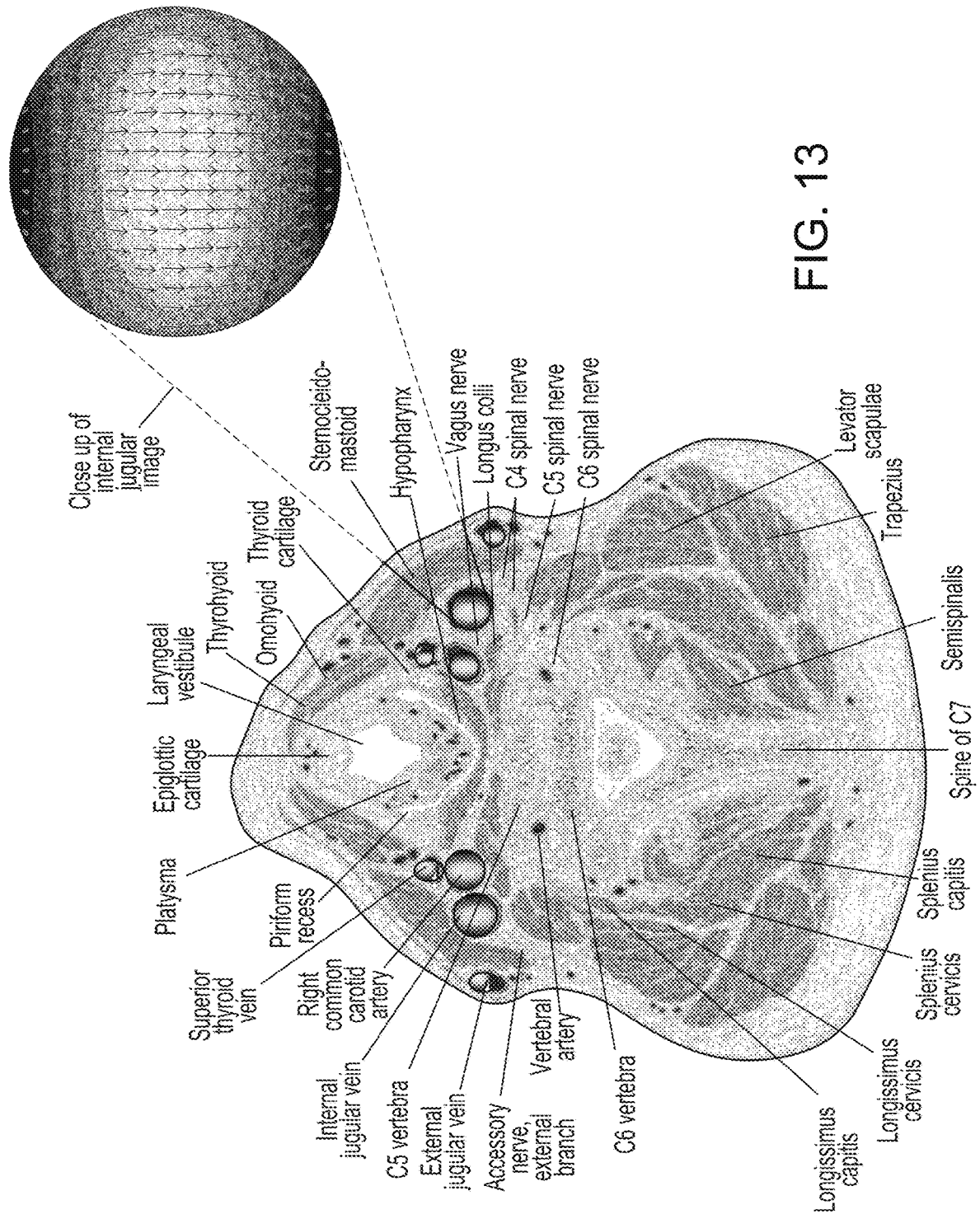
FIG. 13 is a cross sectional view of the neck with its associated blood vessels with cross-sectional views of the distribution of electric fields within blood vessels in the neck.

The two-dimensional internal voltage and electric field (E-field) distributions can be represented as a tomographic image in which the intensity of each image element (e.g., each pixel) is related to the blood flow velocity through that image element. FIGS. 12 and 13 show cross sectional views of the local E-field intensity and direction in an example blood vessel in the presence of a transverse magnetic field.

The tomographic image can be analyzed to estimate the dipole distribution and intensity in the neck (176). If the locations of the blood vessels in the neck are known, the dipole distribution and intensity for each blood vessel in the neck can be determined, and hence the flow rate through each blood vessel can be calculated.

Since the anatomy of each patient is similar but slightly different, the relative—though not exact—positions of the jugular veins and the carotid and vertebral arteries are known beforehand for all patients. These relative positions can be obtained from an anatomical reference, such as CT slices or MRI images for the cross-sectional location corresponding to the position of the collar when placed on the patient. The relative positions can be determined based on the anatomy of each of a collection of patients, and the position of each blood vessel can be represented as a statistical distribution. "Candidate" regions of possible locations for each blood vessel can be identified using a template matching method and validated against a statistical distribution of the blood vessel locations determined based on the anatomy of multiple patients. In some examples, template matching techniques such as Active Appearance Model, as proposed by Cootes in IEEE Transactions on Pattern Analysis and Machine Intelligence, Vol. 23, No. 6, June 2001, the contents of which are incorporated herein by reference in their entirety, can be employed to allow for more accurate deformations as well as better use of specific a priori image knowledge.

In some examples, the tomographic images of the two-dimensional E-fields can be analyzed by image analysis processes to determine the dipole distribution and intensity in the neck. For instance, image analysis processes can include image-based template matching techniques such as Radon or Hough transform-based template matching techniques, as described in "Template Matching Techniques in Computer Vision: Theory and Practice," Roberto Brunelli, Wiley and Sons, 2009, the contents of which are incorporated herein by reference in their entirety. The template can be configured to detect a circular electric dipole such as the dipole shown in FIGS. 12 and 13. Deformable templates using the methods described above can be employed with a feature set distance to be minimized including elements such as radius, intensity, ellipsoid radii, dipole moment, or other elements.

Using both the tomographic images of the electric field distribution in the neck at a given instant in time and the determined or estimated locations of the blood vessels in the neck, image analysis processes can be used to determine the flow rate through each individual blood vessel. For instance, template matching, e.g., using Active Appearance Model techniques, is used for each individual vessel in more detail, to determine the best feature vector including such elements as radius, intensity, ellipsoid radii, dipole moment, or other elements. Using techniques such as logistic regression, support vector machines (SVM), or other estimation techniques, the feature vector, or vessel image estimate itself in the form of a graphical representation, for each vessel of interest, is input to an estimator, such as a logistic regression equation, an SVM, a neural network, or another type of estimator. The estimator outputs the flow rate, at the instant of time, for that particular vessel. In some examples, this process can be repeated at intervals small enough such that the cumulative flow through a blood vessel can be calculated from multiple flow rate estimates for each vessel, and the total flow into the brain can be calculated from the sum of the flows through each individual blood vessel.

The blood flow into the brain can be calculated by $$\text{Total Instantaneous Brain Flow } (t) = \Sigma_{i=1}^{i=N} \phi_i(t),$$

where $\phi_i$ is the flow in the ith blood vessel connected to the brain, N is the number of blood vessels for which blood flow is to be calculated (e.g. the jugular, vertebral, and carotid vessels), and t is time.

Total Instantaneous Brain Flow (TIBF) is a flow rate (flow volume per unit of time). Brain Flow Volume (BFV) is a flow volume and can be obtained by integrating TIBF. BFV can be calculated as a minute flow volume, in which the current averaged TIBF is extrapolated to a period of time such as one minute. In some examples, BFV can be calculated using a period of time of one chest compression cycle, such that the units of measure for BFV are flow volume per compression, per multiple compressions, or per a portion of a compression. BFV can be an instantaneous measure of flow volume or can be averaged.

When BFV is calculated on a per-compression basis, the timing of the interval over which blood flow is to be calculated can be based on the timing of chest compressions delivered to the patient during CPR. A sensor can detect the timing of chest compressions. The sensor can be a motion sensor, such as a motion sensor placed on or under a rescuer's hands or on the patient's chest; a pressure sensor, such as a pressure sensor placed under the rescuer's hands, a camera positioned such that still or video images of CPR delivery can be obtained.

In some examples, BFV can be calculated over an entire compression interval. In some examples, BFV can be calculated for only a portion of a compression interval, the downstroke portion of the compression interview or the release portion of the compression interval. In some examples, there may be a delay interval between the compression interval and measurement of the TIBF. Time delays between the compression interval and TIBF measurement (e.g., as determined by a difference between a fiducial of the compression interval and a time fiducial on the TIBF waveform) can be measured to determine vascular dynamics, for instance by using transit velocity or another approach to estimate vascular features such as compliance or resistance.

In some examples, the blood flow through a subset of all blood vessels in the neck can be determined, for instance to measure the internal vs. external vessel flow, flow through veins vs. arteries, flow through vertebral arteries vs carotid arteries, or other subsets of blood vessels in the neck.

In some examples, the approach to determining blood flow through a patient's neck can be performed by sensing other types of signals, such as acoustic signals or ultrasound signals. For instance, a support component wrapped around at least a portion of a patient's neck (e.g., the collar 100) can include an output generator and a sensor. The output generator applies an output to the neck of the patient, such as a magnetic output, an acoustic output, an ultrasound output, or another type of output. The sensor, such as an electrode, an acoustic sensor, an ultrasound sensor, or another type of sensor, detects a signal in the patient's neck responsive to the output applied by the output generator. Based on the detected signal, the blood flow through some or all of the blood vessels in the patient's neck can be determined using approaches such as described above.

In some embodiments, Doppler ultrasound may be used a measuring tool for employing high frequency sound waves to determine the amount of blood flow through the neck of the patient. For example, an ultrasonic transducer may be provided at the neck of the patient and provided as an output generator and a sensor. The transducer may send and receive sound waves that are amplified through a microphone. The sound waves are reflected off objects, e.g., blood cells, such that the movement of the blood cells causes a change in pitch of the reflected sound waves, i.e., Doppler effect. For instance, when there is no blood flow, the pitch in reflected sound does not change. The information from the reflected sound waves can be processed to determine the flow of blood through the neck.

As described in U.S. Publication No. US2014/0039291, entitled "Arterial and Venous Blood Metrics," filed Aug. 1, 2013, which is incorporated herein by reference in its entirety, for some examples, an internal probe can measure the internal voltage in the neck. The measurement of the internal voltage can be combined with the external voltage measurements enabled by the collar 100, or other suitable apparatus, in order to achieve better accuracy and resolution for the determination of blood vessel location and size and for the estimation of blood flow through each blood vessel.

Figure 14:
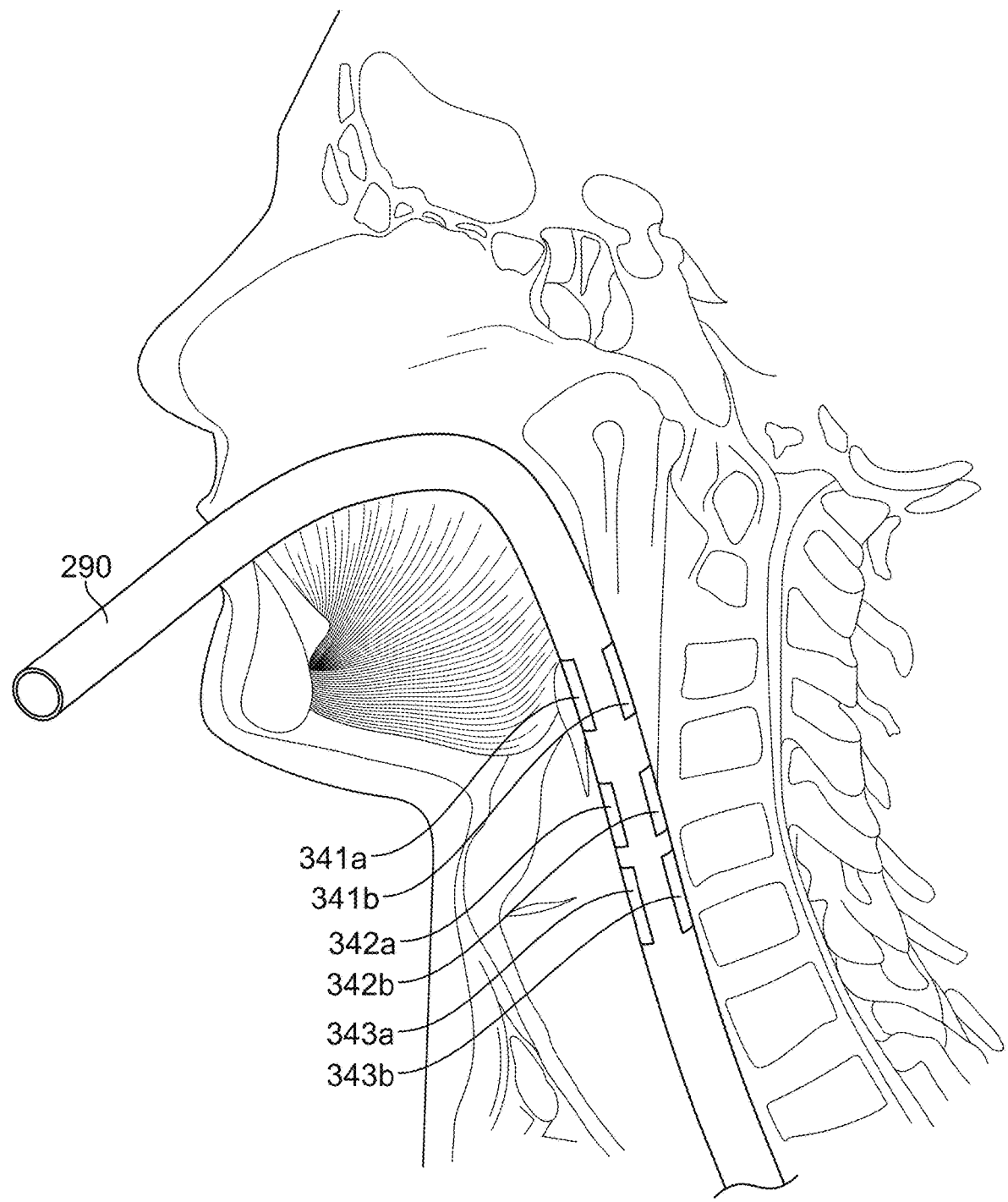
FIG. 14 is a cross-sectional view of the neck with a probe inserted into the esophagus.

FIG. 14 illustrates a probe 240 that can be inserted into the pharynx, esophagus or trachea of the patient. The probe 240 has at least two electrodes approximately circumferentially disposed on its exterior surface positioned on the probe 240 such that the electrodes come into contact with the interior surface of the pharynx, esophagus or trachea when the probe 240 is inserted therein. The electrodes can be any type of electrode suitable for use inside the body of a patient. The electrodes can be mounted to an external surface of the probe 240 or integrated therein. The probe can be inserted into the pharynx, esophagus or trachea such that the electrodes are located in the region of the neck at the level of the T1/T2 and C1-C7 vertebrae.

In some examples, the probe can include one or more sets of electrodes each positioned at a different distance along the length of the probe. Each set of electrodes can include one or more electrodes. In the example of FIG. 14, the probe 240 includes multiple sets of two electrodes 341a and 341b, 342a and 342b, and 343a and 343b disposed at spaced apart positions along the length of the probe 240, the electrodes in each pair may be disposed at approximately diametrically opposed positions around the circumference of the probe 240. In some examples, only a single electrode (e.g., only electrodes 341a, 342a, 343a) can be provided at each position along the length of the probe 240 rather than the pairs of electrodes shown in FIG. 14. In some examples, the probe can include only a single electrode (e.g., only electrode 342a). The use of multiple electrodes disposed in spaced apart positions along the length of the probe 240 permits impedance measurements to be made in multiple axes. Additional information about the probe can be found in US2014/0039291, entitled "Arterial and Venous Blood Metrics," discussed above.

Using impedance tomographic approaches described above, the combination of the probe 240 with the collar 100 can enable blood vessel location and size and blood flow estimations to be determined with better accuracy and resolution.

In some examples, the probe can include an imaging capability that can be used to detect the positions of the blood vessels within the neck of the patient, which can help to improve the accuracy of the impedance tomographic approaches described above. For instance, the probe can be an ultrasound probe In some examples, the measured blood flow to the brain of a patient can be compared to a threshold blood flow. The comparison can be performed automatically by a computing device, such as a defibrillator, a mobile computing device, a remote computing device, or another computing device. If the measured blood flow to the brain of the patient is less than the threshold, the patient's cardiac output is too low, and feedback can be provided to a rescuer treating the patient. For instance, the rescuer can be alerted that the patient's cardiac output is low or instructed to deliver deeper or more rapid chest compressions to the patient in order to increase the cardiac output. The feedback can be provided substantially in real time, e.g., such that the rescuer is provided with the feedback as soon as the patient's cardiac output drops below the threshold. The real time nature of the measurements and feedback enable the rescuer to deliver CPR effectively in accordance with the physiological status of the patient. In some examples, referring again to FIG. 4, the measured blood flow can be displayed on a display interface of the control device 140.

In some examples, the measured or estimated blood flow to the brain of a patient can be stored for future use, e.g., by a physician who later treats the patient.

In some examples, the blood flow to the brain of a patient can be monitored over a period of time in which the patient is not receiving CPR. For instance, a patient with inconsistent cardiac output can wear the collar 100, or another suitable apparatus, for a period of time (e.g., an hour, a day, or another period of time) in order to obtain data indicative of the patient's blood flow over time.

Referring again to FIGS. 4 and 6, the control device 140 can be connected to the collar 100 or other apparatus via a cable 142. The control device 140 can be powered by a power supply 172, such as a battery 174 or an external power source. The control device 140 can have a communications module 176 that enables the control device 140 to communicate with other computing devices. For instance, the communications module 176 can include wireless Internet capability 178, Ethernet connection capability 180, cellular communications capability, or other types of communication. The control device 140 can have a user input module 164, such as a keyboard, a touch screen, an audio input module, a video input module, a mouse, or another type of user input capability; and a display module 166, such as a display screen, an audio output module, or another type of display or output capability. In some cases, the user input module 164 and the display module 166 both make use of the same display screen. The control device 140 can include program memory 168 and dynamic random access memory (DRAM) 170.

In some embodiments, the control device 140 may be made up of the Lorentzian Flow Tomography (LFT) driver/sensing electronics as depicted in FIG. 6 in combination with a second computing device, such as a computer, a mobile computing device (e.g., a mobile phone, a tablet, a wearable computing device such as a watch or glasses, a personal digital assistant (PDA)), a defibrillation device, or another type of computing device. The LFT driver/sensing electronics may be housed separately from the second computing device. The circuitry and software used for controlling the LFT drivers, and processing the signals measured by the LFT sensing electronics may be part of the second computing device. The two devices may communicate via a wire control such as USB or wirelessly such as via 802.11 WiFi.

Other embodiments are within the scope of the following claims.

What is claimed is:

1. A system for determining blood flow to and from the brain of a patient comprising:
   at least one output generator configured to be positioned adjacent to the neck of the patient and having a current source and two or more magnetic coils configured to generate a time-varying magnetic field at the neck of the patient;
   at least one sensor configured to be positioned adjacent to the neck of the patient, the at least one sensor configured to detect a voltage or an electric field induced responsive to the time-varying magnetic field and blood flow through the neck of the patient;
   a support component for holding the at least one output generator and the at least one sensor at the neck of the patient; and
   a processor with a memory, a power supply and other processing components, the processor being configured to estimate a distribution of the voltage or the electric field, and to estimate blood flow through the neck based at least in part on the estimated distribution of the voltage or electric field.

2. The system of claim 1, wherein the two or more magnetic coils are configured to be located at diametrically opposite positions around the neck of the patient.

3. The system of claim 1, wherein the two or more magnetic coils are configured to generate a magnetic field that is substantially spatially uniform across the neck of the patient.

4. The system of claim 1, wherein the two or more magnetic coils are configured to generate a time-varying magnetic field having a period of between about 10 and about 100 milliseconds.

5. The system of claim 1, wherein the at least one sensor is disposed between at least two of the two or more magnetic coils.

6. The system of claim 1, wherein the at least one sensor comprises a plurality of electrodes configured to be in electrical contact with the neck of the patient.

7. The system of claim 6, wherein the plurality of electrodes comprises three or more electrodes.

8. The system of claim 6, wherein one of the plurality of electrodes is configured to be used as a reference electrode while the remaining electrodes are configured to be current sources, the induced voltages being measured on each electrode while the current is being delivered.

9. The system of claim 6, wherein the plurality of electrodes are configured to detect a voltage induced across the neck of the patient responsive to the applied output.

10. The system of claim 1, wherein the processor is configured to estimate blood flow from two or more blood vessels in the neck based at least in part on the estimated distribution of the voltage distribution.

11. The system of claim 1, wherein the processor is configured to estimate at least a two-dimensional distribution of the voltage within the neck of the patient.

12. The system of claim 1, wherein the processor is configured to estimate net blood flow into the brain based at least in part on the estimated distribution of the voltage distribution and a difference between estimated blood flowing into the brain and estimated blood flowing out of the brain.

13. The system of claim 1, wherein the processor is configured to determine a location of each of one or more blood vessels in the neck of the patient based on the voltage distribution, an expected location of each of the one or more blood vessels, and an impedance distribution in the neck of the patient.

14. The system of claim 13, wherein the processor is configured to provide a tomographic image indicative of the impedance distribution in the neck of the patient.

15. The system of claim 14, wherein the tomographic image comprises a plurality of pixels, each pixel having an intensity proportional to a measured velocity of blood flow through a portion of the neck of the patient corresponding to the pixel.

16. The system of claim 1, wherein the processor is configured to estimate at least one of an instantaneous measure of blood flow through one or more blood vessels and an average measure of blood flow through each of the one or more blood vessels over a period of time.

17. The system of claim 16, wherein the period of time comprises a duration of a chest compression or a portion of a chest compression applied to the chest of the patient.

18. The system of claim 1, comprising a defibrillator comprising at least one of the processor, the memory, the power supply, and the other processing components.

19. The system of claim 1, comprising at least one of a computing device, a tablet, a mobile device, a PDA, and a cellular phone that comprises at least one of the processor, the memory, the power supply, and the other processing components.

20. The system of claim 1, wherein the support component comprises a flexible sheet configured to support the at least one output generator adjacent to the neck of the patient.

21. The system of claim 20, wherein the flexible sheet is configured to wrap around at least a portion of the neck and to be supported by the neck, and comprises ends configured to attach to each other for the flexible sheet to form a collar.

22. The system of claim 1, comprising at least one of an acoustic sensor and an ultrasound sensor.

23. The system of claim 1, wherein the processor is configured to provide an image of blood flow through the neck of the patient based on the signal responsive to an output applied by the output generator and blood flow through the neck of the patient.

24. The system of claim 1, wherein the two or more magnetic coils comprise a plurality of sets magnetic coils configured to apply a sequenced magnetic field to the neck of the patient.

25. The system of claim 24, wherein the two or more magnetic coils are configured to generate the at least one magnetic field orthogonal to the neck of the patient responsive to current supplied by the current source.

26. The system of claim 1, wherein the processor is configured to estimate the distribution of the electric field within the neck of the patient based at least in part on image-based template matching techniques.

27. The system of claim 1, wherein the processor is configured to estimate the distribution of the electric field within the neck of the patient as an inverse problem.

28. A system for determining blood flow to and from the brain of a patient, the system comprising:
   circuitry for controlling at least one output generator to apply an output to the neck of the patient;
   circuitry for sensing and measuring a signal detected by at least one sensor responsive to the applied output and blood flow through the neck of the patient, the signal comprising a voltage or an electric field induced responsive to the time-varying magnetic field and blood flow through the neck of the patient; and
   a processor with a memory, a power supply and other processing components, the processor performing operations comprising:
      estimating at least a two-dimensional distribution of the signal within the neck of the patient, and
      estimating a blood flow through the neck based at least in part on the estimated signal distribution.

29. The system of claim 28, wherein the circuitry for controlling the at least one output generators comprises circuitry for controlling a plurality of magnetic elements configured to apply a magnetic field to the neck of the patient.

30. The system of claim 28, wherein the circuitry for sensing and measuring the signal comprises circuitry for sensing and measuring an induced voltage across the neck of the patient detected by electrodes.

31. The system of claim 30, wherein the processor is for estimating at least a two-dimensional distribution of the induced voltage within the neck of the patient, and estimating a blood flow through the neck based at least in part on the at least a two-dimensional distribution of the induced voltage.

32. The system of claim 28, wherein the processor is configured to estimate a three-dimensional distribution of the signal within the neck of the patient.

33. The system of claim 28, wherein the processor is configured to estimate net blood flow into the brain based at least in part on the estimated signal distribution.

34. The system of claim 28, wherein the processor is configured to determine a location of each of one or more blood vessels in the neck of the patient based on the signal distribution.

35. The system of claim 34, wherein the processor is configured to determine the location of each of the one or more blood vessels based at least in part on an impedance distribution in the neck of the patient.

36. The system of claim 35, wherein the processor is configured to provide a tomographic image indicative of the impedance distribution in the neck of the patient.

37. The system of claim 36, wherein the tomographic image comprises a plurality of pixels, each pixel having an intensity proportional to the velocity of blood flow through a portion of the neck of the patient corresponding to the pixel.

38. The system of claim 28, wherein the processor is configured to determine an instantaneous measure of blood flow through each of the one or more blood vessels.

39. The system of claim 28, wherein the processor is configured to determine an average measure of blood flow through one or more blood vessels over a period of time.

40. The system of claim 39, wherein the period of time comprises a duration of a chest compression or a portion of a chest compression applied to the chest of the patient.

41. The system of claim 28, comprising a defibrillator comprising at least one of the processor, the memory, the power supply, and the other processing components.

42. The system of claim 28, comprising at least one of a computing device, tablet, mobile device, PDA and cellular phone that comprises at least one of the processor, the memory, the power supply, and the other processing components.

* * * * *

UNITED STATES PATENT AND TRADEMARK OFFICE
CERTIFICATE OF CORRECTION

PATENT NO. : 10,874,315 B2
APPLICATION NO. : 15/468924
DATED : December 29, 2020
INVENTOR(S) : Gary A. Freeman Page 1 of 1

It is certified that error appears in the above-identified patent and that said Letters Patent is hereby corrected as shown below:

On the Title Page

Column 1, Line 1, item (56) under "OTHER PUBLICATIONS", delete ""Theorectical" and insert -- "Theoretical --

In the Claims

Column 21, Line 24, Claim 29, delete "generators" and insert -- generator --

Signed and Sealed this
Ninth Day of March, 2021

Drew Hirshfeld
*Performing the Functions and Duties of the*
*Under Secretary of Commerce for Intellectual Property and*
*Director of the United States Patent and Trademark Office*